United States Patent [19]

Fujita

[11] 4,354,833
[45] Oct. 19, 1982

[54] ORTHODONTIC APPLIANCE

[76] Inventor: Kinya Fujita, No. 326, Nagasawa, Yokosuka-shi, Kanagawa-ken, Japan

[21] Appl. No.: 216,737

[22] Filed: Dec. 15, 1980

[30] Foreign Application Priority Data

Aug. 8, 1980 [JP] Japan .......................... 55/112498[U]

[51] Int. Cl.³ .............................................. A61C 3/00
[52] U.S. Cl. ................................................... 433/20
[58] Field of Search ............................ 433/20, 8, 140

[56] References Cited

U.S. PATENT DOCUMENTS

| 1,082,052 | 12/1913 | Strang | 433/20 |
| 1,361,661 | 12/1920 | Alexander | 433/20 |
| 1,395,922 | 11/1921 | McCarter | 433/20 |
| 1,622,856 | 3/1927 | Angle | 433/8 |
| 2,566,414 | 9/1951 | Henry | 433/20 |
| 3,302,288 | 2/1967 | Tepper | 433/20 |
| 3,842,503 | 10/1974 | Wildman | 433/24 |
| 4,209,906 | 7/1980 | Fujita | 433/11 |

FOREIGN PATENT DOCUMENTS 570882 2/1933 Fed. Rep. of Germany ........ 433/20

OTHER PUBLICATIONS

"IP" Laboratories Catalog, Preformed Arch Wires, p. 31, 1974.
"Unitek" Catalog Pre-Formed Arches, 1962.

Primary Examiner—Gene Mancene
Assistant Examiner—John J. Wilson
Attorney, Agent, or Firm—Blanchard, Flynn, Thiel, Boutell & Tanis

[57] ABSTRACT

The present invention relates to an orthodontic appliance for the treatment of dental malocclusion from the internal sides of teeth, that is, the lingual or palatal side. Brackets are used in the present invention for securing the orthodontic wire, and are provided with grooves so that the orthodontic procedure is carried out by means of the elasticity of the wire. A preshaped orthodontic wire is provided which is arch-shaped along the central incisors, side incisors and canines, linear along the molars and premolars, and where the canines and first premolars meet, it is bent in a crank-shape. Introduction of a crank in the orthodontic wire during manufacture simplifies the orthodontic procedure. Individual slight differences in orthodontic procedure that occur in different persons can be accommodated by slight adjustments of the wire of the invention.

5 Claims, 18 Drawing Figures

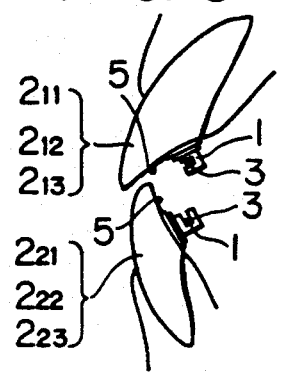
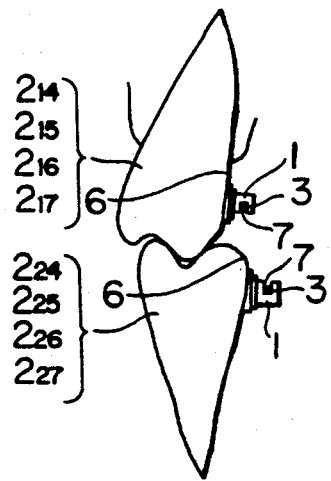
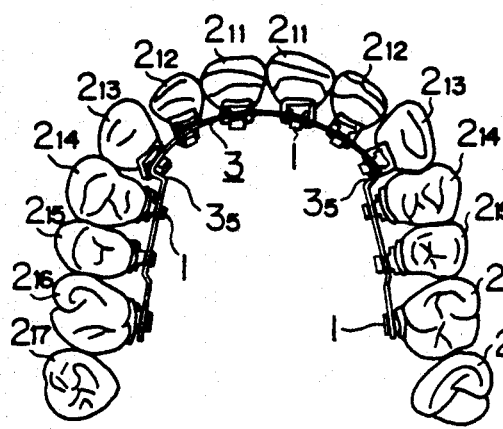
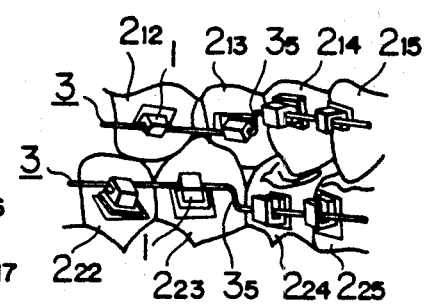

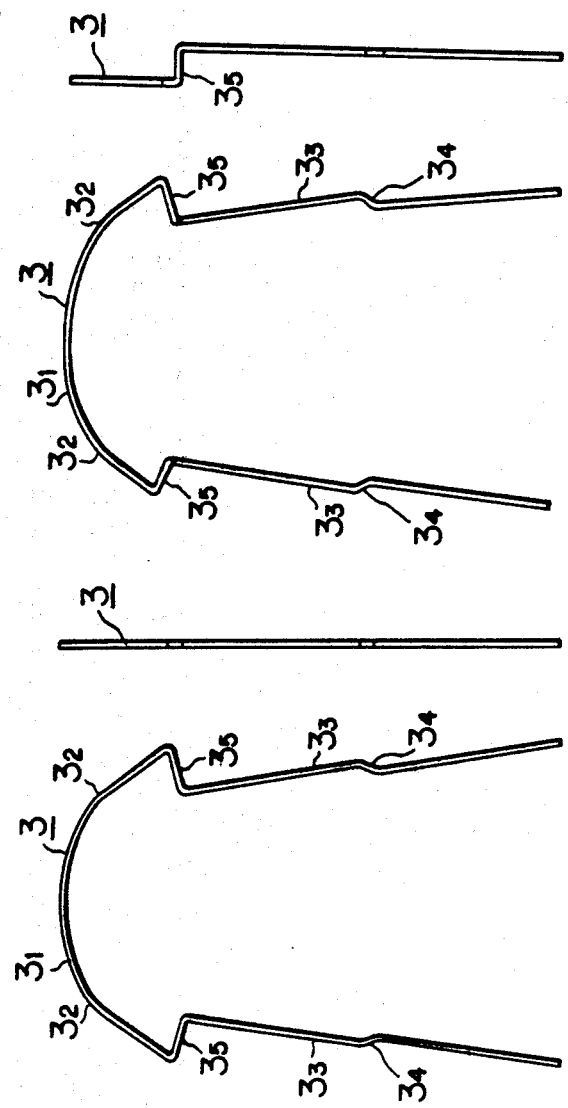

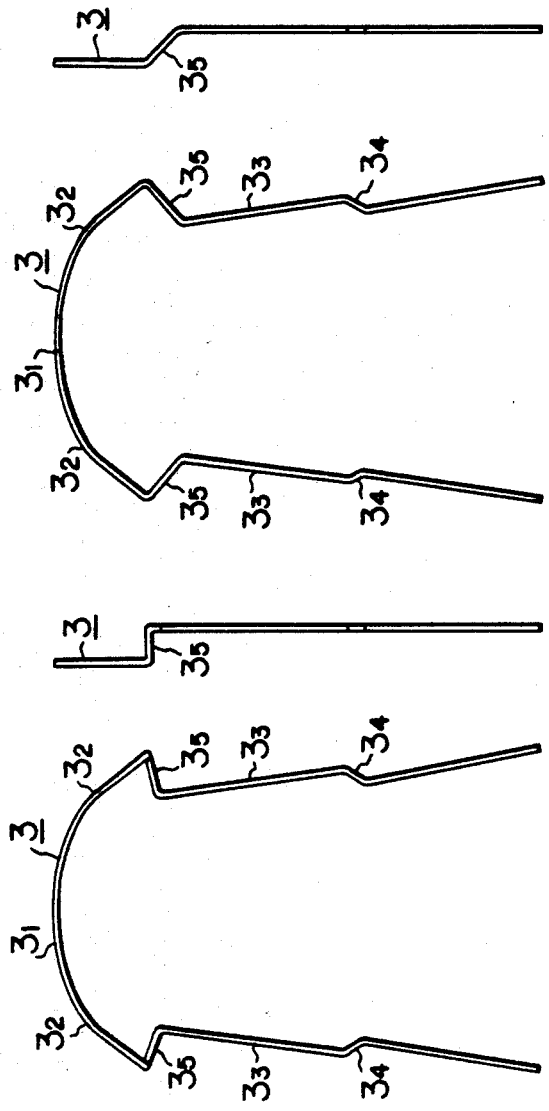

ORTHODONTIC APPLIANCE

The present invention relates to an orthodontic appliance for use in the treatment of dental malocclusion, particularly to the shape of orthodontic wire used in the appliance.

The newest and the most effective method of orthodontic treatment, the main purpose of which to treat dental malocclusion, is the technique of firmly fixing a bracket (1) for a fixing wire to each tooth (2) and inserting a fixing wire (3) into each bracket (1) and fixing it to the brackets in order to correct a malalignment of the teeth (2) by means of the elastic force of the wire (3). For example, as shown in FIG. 2, when the upper jaw central incisor ($2_{11}$) protrudes abnormally towards the outside as shown by the solid line, it is corrected to the state shown by the broken line by a method in which a band (4) is applied to each tooth ($2_{11}$) and brackets (1) are welded to the outside of these bands (4). Then a curved orthodontic wire (3) is fixed in turn to each of these brackets (1) to correct teeth malalignment by the elastic force of this wire (3).

The main disadvantage of the conventional method is that the brackets (1) and wire (3) are clearly visible from the outside of the mouth when the mouth is opened, because the brackets (1) are bonded or welded to the outer surfaces of the teeth (2). To improve facial beauty during orthodontic procedures, the inventor devised an orthodontic appliance wherein brackets are bonded or welded on the internal faces of the teeth without need for bands. This appliance is disclosed in U.S. Pat. No. 4,209,906 and a Japanese patent has been applied for (Japan patent application No. S 51-155429). In this previous invention the brackets and wire are hidden, and the appliance reduces a considerable psychological burden on patients.

However, installation of the brackets on the inner faces of the teeth intails certain disadvantages. The curve of the dental arch along the outer sides of the teeth is nearly elliptical, and the outer surfaces of the teeth are nearly perpendicular so that the orthodontic wire is simply bent to an elliptical shape when the wire is applied to the teeth. On the other hand, the curve along the inner sides of the teeth is not a simple curve. The angles of the lingual surfaces of inner central incisor, side incisors and canines, as shown in FIG. 3, are sloped not perpendicular. When a bracket is installed, it is located close to the gingiva so as not to disturb the occlusion, and the slope of the teeth at these locations is more flat than it is at locations farther from the gingiva. By contrast, the slopes of the lingual surfaces of the 1st and 2nd premolars and the 1st and 2nd molars are nearly perpendicular. Because of this difference in slope, proper orthodontic treatment with an internal appliance cannot be achieved simply by bending the orthodontic wire in an elliptical shape.

SUMMARY OF THE INVENTION

The primary purpose of the present invention is to facilitate the installation of orthodontic brackets on the insides of the teeth, and the orthodontic wire requires only minimum adjustment according to the individual differences and degree of orthodontic procedure.

The second purpose of the present invention is to make easy exchanging of the wire in applying and removing it for the purposes of the orthodontic procedure.

Additional purposes and advantages of the present invention will be clarified by the following explanation of the drawings.

BRIEF DESCRIPTION OF THE DRAWINGS

FIG. 3 illustrates an occlusion state of the incisors.

FIG. 4 illustrates an occlusion state of the molars.

FIG. 5 illustrates the method of orthodontic procedure using the appliance of the present invention.

FIG. 6 illustrates an occlusion state of teeth on the upper jaw and the lower jaw utilizing the appliance of the present invention.

FIGS. 7, 7(a), 7(b) and 7(c), FIGS. 8, 8(a), 8(b) and 8(c), FIGS. 9, 9(a), 9(b) and 9(c), and FIGS. 10, 10(a), 10(b) and 10(c) are plan views, the right-side views and top views in the first, second, third and fourth detailed embodiments of the invention, respectively.

DETAILED DESCRIPTION

Figure 1:
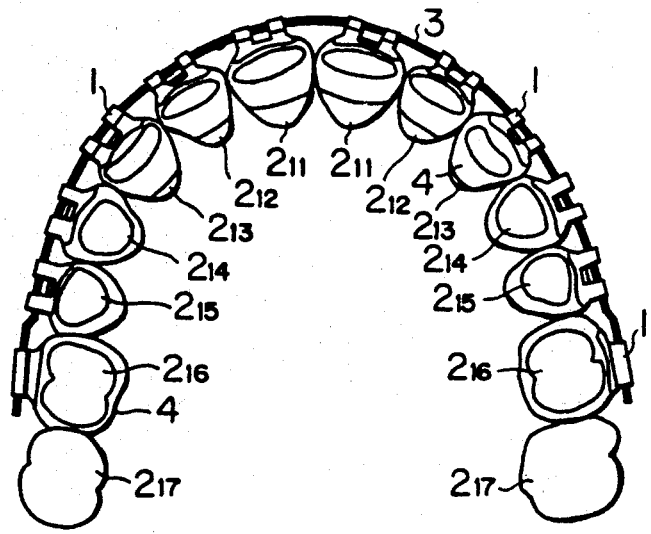
FIG. 1 is an illustration of a conventional orthodontic treatment technique.
Figure 2:
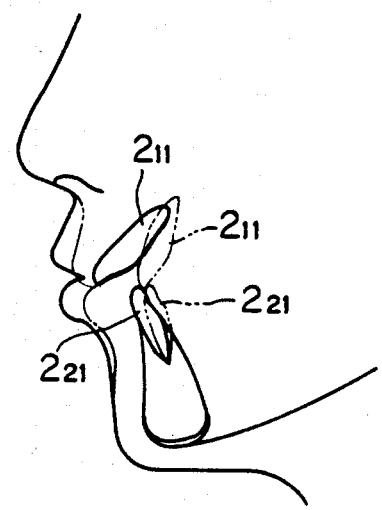
FIG. 2 illustrates the states of teeth before and after the orthodontic treatment.

The embodiments of the present invention will be explained with reference to the drawings.

FIG. 5 illustrates the dental alignments of the upper jaw, wherein ($2_{11}$) ($2_{11}$) are the central incisors, ($2_{12}$) ($2_{12}$) are the side incisors, ($2_{13}$) ($2_{13}$) are canines, ($2_{14}$) ($2_{14}$) are the first premolars, ($2_{15}$) ($2_{15}$) are the second premolars, ($2_{16}$) ($2_{16}$) are the first molars, and ($2_{17}$) ($2_{17}$) are the second molars. The overall shape of a line connecting the entire alignment of the teeth is elliptical. The dental alignments of the lower jaw are almost the same as those of the upper jaw, and an illustration of the lower jaw is therefore omitted.

When orthodontic procedures according to the present invention are carried out, an orthodontic wire (3) is fixed to brackets (1) on each tooth. The general arrangement orthodontic alignment is that teeth on the upper jaw occlude with and protrude slightly outside of the teeth on the lower jaw. Thus, in order to prevent any disturbance of the occlusion by the brackets (1), the brackets (1) are installed in positions as close to the gingiva as possible. The sloped inside surfaces (15) of the central incisors ($2_{11}$) ($2_{11}$), side incisors ($2_{12}$) ($2_{12}$) and canines ($2_{13}$) ($2_{13}$) are installed with brackets (1), and the perpendicular inside surfaces (6) of the first premolars ($2_{14}$) ($2_{14}$), the second premolars ($2_{15}$) ($2_{15}$), the first molars ($2_{16}$) ($2_{16}$) and the second molars ($2_{17}$) ($2_{17}$) are also installed with brackets (1). Orthodontic wire (3) is fixed to the molars ($2_{16}$) ($2_{16}$), ($2_{17}$) ($2_{17}$) as the anchors, so that both ends of the wire (3) are fixed to rings on the teeth, and then the brackets are bonded.

The brackets (1) are installed in such a manner that the wire insertion grooves (7) do not form a smooth elliptical line, but rather define several sharp angular sections. The orthodontic wire (3) should be made so that the wire can be applied along the exact alignment of the teeth as needed for correct connection and orthodontic procedures.

FIGS. 7, 7(a), 7(b), 7(c) illustrate the preshaped orthodontic wire (3). The shape of the wire where it connects the central incisors ($2_{11}$) ($2_{11}$), side incisors ($2_{12}$) ($2_{12}$) and canines ($2_{13}$) ($2_{13}$) is an arch ($3_1$) of nearly uniform curvature, but the section ($3_2$), where the side incisors ($2_{12}$) ($2_{12}$) and canines ($2_{13}$) ($2_{13}$) meet is bent slightly inwardly. The section ($3_3$) corresponding to the place where the first premolars ($2_{14}$) ($2_{14}$) and the second premolars ($2_{15}$) ($2_{15}$) meet and the first molars ($2_{16}$) ($2_{16}$) and the second molars ($2_{17}$) ($2_{17}$) meet is almost linear ($3_3$), but the section ($3_4$) where the second premolars ($2_{15}$) ($2_{15}$) and the first molars ($2_{16}$) ($2_{16}$) meet is bent in a slightly inclined shape. The section ($3_5$) where the canines ($2_{13}$) ($2_{13}$) and the first premolars ($2_{14}$) ($2_{14}$) meet, is bent in a crank shape. This bent section ($3_5$), as illustrated in FIGS. 7, 7(a), 7(b), 7(c), is in the same plane as the arch ($3_1$), the bent section ($3_2$), the linear section ($3_3$), and the bent section ($3_4$) and the line connecting these sections.

As illustrated in FIGS. 8, 8(a), 8(b), 8(c), the wire at the bent sections ($3_5$) is bent first inwardly at the ends of the arch ($3_1$), in the same plane as the arch, then is bent perpendicularly to this plane, and then bent horizontally to form bent section connecting the arch ($3_1$) and the linear section ($3_3$).

As illustrated in FIGS. 9, 9(a), 9(b), 9(c), the wire is bent first in a direction perpendicular to the plane of the arch ($3_1$), then is bent inwardly and horizontally, and then bent again to form a bent section connecting the arch ($3_1$) and a linear section ($3_3$).

As illustrated in FIGS. 10, 10(a), 10(b), 10(c), the wire is bent such that it connects the plane of the curved arch ($3_1$) and the linear section ($3_3$), so that the bent section ($3_5$) slopes directly between these sections.

The examples of the detailed descriptions above are given for the alignment of the teeth of the upper jaw ($2_{11}$)–($2_{17}$), but the examples also apply to the alignment of the teeth of the lower jaw ($2_{21}$)–($2_{27}$).

The shape of the orthodontic wire may be altered within the range of the claims in the present invention. The brackets may be ones other than the brackets used in the examples of the description.

What I claim is:

1. In an orthodontic appliance for correcting dental malocclusion comprising a one-piece preshaped orthodontic wire, a plurality of brackets adapted to be affixed to the lingual surfaces of the teeth of the dental arch of a patient, said dental arch comprising central incisor, side incisor, canine, first premolar, second premolar and first molar teeth, said orthodontic wire being adapted to be secured to and apply force against said brackets so that said orthodontic wire is effective for changing the positions of the teeth, the improvement which comprises: said orthodontic wire comprises a central arch-shaped section having a substantially uniform curvature corresponding to the desired curvature of the central portion of the dental arch of the patient consisting of the lingual surfaces of the incisor and canine teeth, a pair of lateral sections, each lateral section being substantially linear and corresponding to a line extending between the lingual surfaces of the premolar and molar teeth with the respective ends of said central arch-shaped portion being horizontally transversely outwardly offset from the adjacent ends of said lateral sections, and a pair of connecting sections connecting the respective ends of said central arch-shaped portion with the adjacent ends of said lateral sections, each connecting section extending transversely inwardly toward the center of said central arch-shaped portion a short distance.

2. An orthodontic appliance as claimed in claim 1 in which said central arch-shaped portion is bent slightly inwardly at locations corresponding to the surfaces of contact between the side incisor teeth and the canine teeth.

3. An orthodontic appliance as claimed in claim 1 or claim 2 in which said lateral sections are bent inwardly at locations corresponding to the surfaces of contact between the second premolar teeth and the first molar teeth.

4. An orthodontic appliance as claimed in claim 1 or claim 2 in which said lateral sections are located in a common plane which is vertically offset from the plane of said central arch-shaped portion and wherein said connecting sections also extend transversely between the planes of said central arch-shaped portion and said lateral sections.

5. An orthodontic appliance as claimed in claim 1 or claim 2 in which said brackets have slots opening toward the occlusion of the teeth of the upper and lower jaws of the patient, said orthodontic wire being received in said slots.

* * * * *

Disclaimer 4,354,833.—*Kinya Fujita*, Yokosuka, Japan. ORTHODONTIC APPLIANCE. Patent dated Oct. 19, 1982. Disclaimer filed June 3, 1985, by the inventor.

Hereby enters this disclaimer to claims 1, 2, 3 and 5 of said patent.
[*Official Gazette July 23, 1985.*]